United States Patent
Wollert et al.

(10) Patent No.: US 10,233,973 B2
(45) Date of Patent: Mar. 19, 2019

(54) LOW-FRICTION SEALING DEVICE AND ROLLING BEARING EQUIPPED THEREWITH

(71) Applicant: Aktiebolaget SKF, Gothenburg (SE)

(72) Inventors: Janek Wollert, Hettstadt (DE); Julian Veeh, Dittelbrunn (DE)

(73) Assignee: Aktiebolaget SKF, Göteborg (SE)

( * ) Notice: Subject to any disclaimer, the term of this patent is extended or adjusted under 35 U.S.C. 154(b) by 0 days.

(21) Appl. No.: 15/470,399

(22) Filed: Mar. 27, 2017

(65) Prior Publication Data
US 2017/0284470 A1 Oct. 5, 2017

(30) Foreign Application Priority Data

Apr. 5, 2016 (IT) .............................. UA2016A2310

(51) Int. Cl.
| | |
|---|---|
| *F16C 33/78* | (2006.01) |
| *F16C 33/80* | (2006.01) |
| *G01N 3/42* | (2006.01) |
| *G01N 25/04* | (2006.01) |

(52) U.S. Cl.
CPC ........ *F16C 33/7886* (2013.01); *F16C 33/805* (2013.01); *G01N 3/42* (2013.01); *G01N 25/04* (2013.01); *G01N 2203/02* (2013.01); *G01N 2203/0202* (2013.01); *G01N 2203/0226* (2013.01)

(58) Field of Classification Search
CPC .. F16C 33/7886; F16C 33/7889; F16C 33/80; F16C 33/805
See application file for complete search history.

(56) References Cited

U.S. PATENT DOCUMENTS

| 8,007,179 | B2* | 8/2011 | Heim | ...................... B60B 27/00 |
|---|---|---|---|---|
| | | | | 384/448 |
| 2013/0127119 | A1* | 5/2013 | Haepp | ................. F16C 33/7863 |
| | | | | 277/351 |
| 2016/0178010 | A1* | 6/2016 | Kaiser | ................... F16C 33/805 |
| | | | | 277/351 |
| 2016/0221391 | A1* | 8/2016 | Lim | .................... B60B 27/0073 |

FOREIGN PATENT DOCUMENTS

| EP | 2685119 A1 | 1/2014 |
|---|---|---|
| EP | 2878842 A1 | 6/2015 |
| KR | 20130087855 A | 8/2013 |
| KR | 20140005546 A | 1/2014 |

* cited by examiner

*Primary Examiner* — James Pilkington
(74) *Attorney, Agent, or Firm* — Bryan Peckjian; SKF USA Inc. Patent Dept.

(57) ABSTRACT

A sealing device for insertion between a first and a second bearing part. The device including a rotating first shield, a stationary second shield, and an elastomeric sealing element having a first and a second sealing lip. The first shield includes a peripheral section having a first and a second axially extending sleeve portion connected by a first radially extending flange portion. The second shield including a support section for the lips, having an intermediate frusto-conical portion that connects a second flange portion of the peripheral section to a mounting section of the second shield. The intermediate portion is positioned axially at a step formed by the first flange portion and by the first sleeve portion. The mounting section is arranged partially inside the second sleeve portion to form an axially directed labyrinth seal that is in metal-to-metal contact with the second bearing.

15 Claims, 1 Drawing Sheet

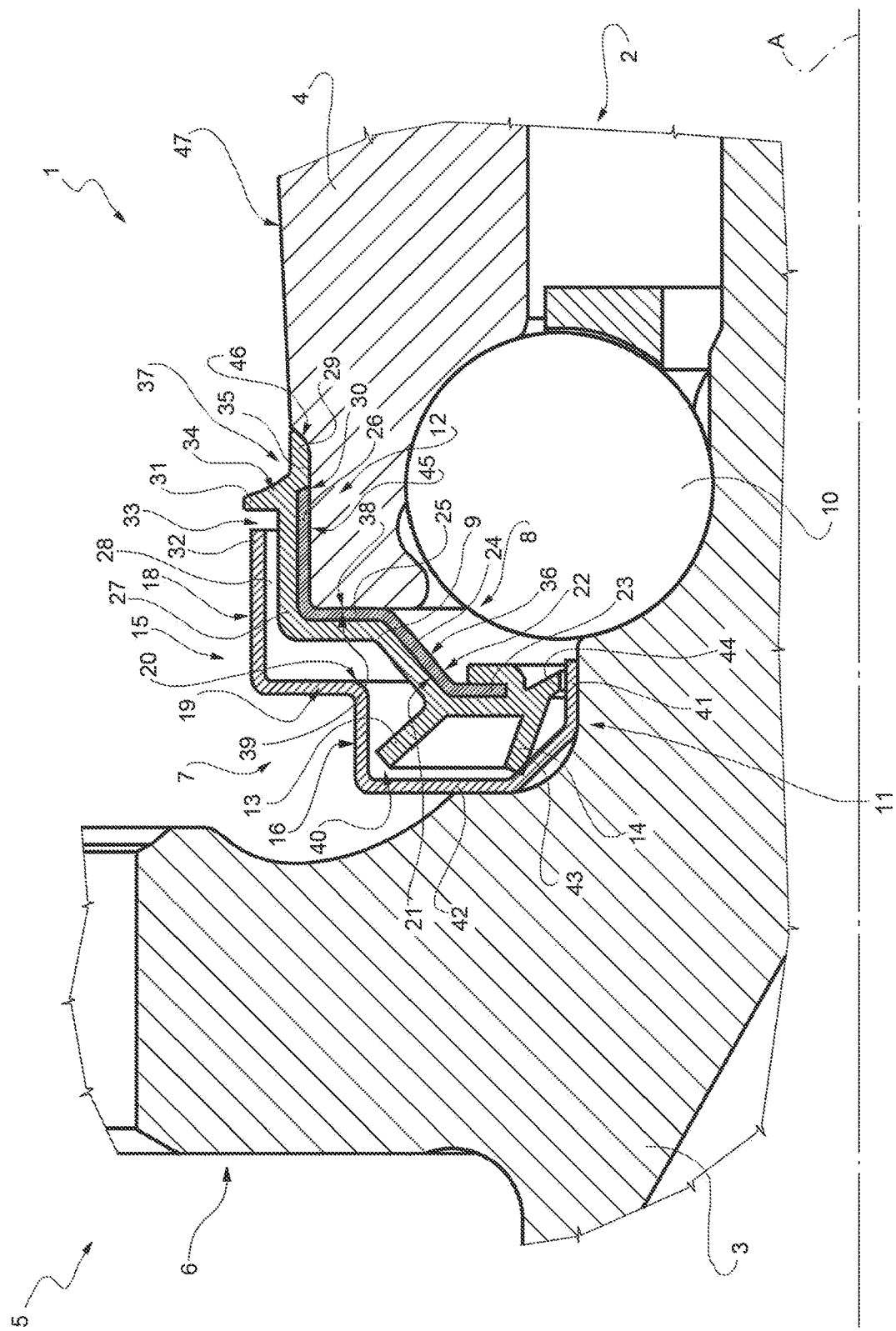

LOW-FRICTION SEALING DEVICE AND ROLLING BEARING EQUIPPED THEREWITH

CROSS REFERENCE TO RELATED APPLICATIONS

This application claims priority to Italian patent application no. 102016000034819 filed on 4 May 2016, the contents of which are fully incorporated herein by reference.

FIELD OF THE INVENTION

The present invention relates to a low-friction sealing device, designed in particular for a rolling bearing of a wheel and hub assembly, and having, in addition to low-friction operation, a simple structure, improved sealing action and reduced overall dimensions. The invention also relates to a rolling bearing which preferably forms a wheel and hub assembly equipped with a low-friction sealing device of aforesaid type and having reduced overall dimensions, particularly in the axial direction, and a reduced weight.

BACKGROUND OF THE INVENTION

A rolling bearing forming a wheel and hub assembly provides an inner ring, which rotates in use, having a flange to support a vehicle wheel, and an outer ring, which is stationary in use; a radial annular space between the inner and the outer ring houses the rolling bodies designed to make the inner and outer ring freely rotatable relative to one another about a common axis of symmetry. To protect the rolling bodies, a sealing device is arranged between the inner and the outer ring on the side of the wheel flange. A suitable sealing device is known from US2013/0127119A1, and provides a first annular shield fixed to the rotating ring and a second annular shield fixed to the stationary ring. The second shield is integrally equipped with an annular elastomeric sealing element designed to exert a static sealing action on the stationary ring and a sliding, or "dynamic", sealing action on the first shield by means of one or more elastic sealing lips projecting from the second shield towards the first shield.

In order to reduce the friction of the seal, provision is typically made to reduce the contact force with the sealing lips, or to reduce the number of sealing lips in contact with the sealing device, but this has a negative effect on the sealing capacity of the device. To reduce or eliminate this problem, a pre-sealing operation is performed in the device to prevent water or mud from reaching the contact sealing lips of the device which provide a sliding seal. However, the implementation of this function requires sufficient space to develop adequate labyrinth seals, resulting in sealing devices such as that of US2013/0127119A1, with rather large overall dimensions.

Moreover, the axial positioning of the sealing lips in contact is frequently affected by the elastic reaction of the elastomer provided in the sealing device to apply the static sealing action, resulting in a contact force of the sealing lips which may be too low or too high, thus rendering the sliding sealing action unreliable.

Finally, the known sealing devices may frequently have a limited static sealing action, particularly in the axial direction; however, the provision of more space causes the rings of the bearing to become larger and heavier.

BRIEF SUMMARY OF THE INVENTION

The object of the present invention is to provide a sealing device for a rolling bearing and a rolling bearing equipped with this sealing device, which are free of the problems described above, and which, in particular, have a reliable low-friction sealing action, for both static and dynamic sealing, and reduced overall dimensions. A further object of the invention is to provide an assembly composed of a rolling bearing and a sealing device, in particular a wheel and hub assembly having a reduced weight.

According to the invention, a sealing device for a rolling bearing and a rolling bearing equipped with this sealing device are provided, particularly for forming a wheel and hub assembly, as defined in the appended claims.

BRIEF DESCRIPTION OF THE SEVERAL VIEWS OF THE DRAWING

Further characteristics and advantages of the present invention will be apparent from the following description of a non-limiting embodiment of the invention, provided with reference to the single FIGURE of the appended drawing, in which:

FIG. 1 shows schematically, in radial section, a longitudinal view of a wheel and hub assembly comprising a rolling bearing and a low-friction sealing device according to the invention.

DETAILED DESCRIPTION OF THE INVENTION

With reference to FIG. 1, the reference numeral 1 indicates the whole of a sealing device for a rolling bearing 2, comprising a first bearing part 3 and a second bearing part 4; in particular, in the non-limiting embodiment shown, the rolling bearing part 3 is equipped, on the opposite side from the bearing part 4, with a wheel flange 6, so that the rolling bearing parts 3 and 4 form a wheel and hub assembly 5. The rolling bearing parts 3 and 4 are made rotatable relative to one another about an axis of symmetry A of the sealing device 1 by means of a plurality of rolling bodies 10 fitted in an annular space between the rolling bearing parts 3 and 4.

The sealing device 1 provides a first annular shield 7, which is preferably made of sheet metal, so as to be relatively rigid, a second annular shield 8, also preferably made of sheet metal so as to be relatively rigid, and an annular sealing element 9 made of an elastomeric material, so as to be elastically deformable, which is supported in an integral way by the second annular shield 8.

The first annular shield 7 has a first mounting section 11 for attachment to the first bearing part 3, and is rotating in use about the axis of symmetry A; the second annular shield 8 is coaxial with the first shield 7 and has a second mounting section 12 for attachment to the second bearing part 4, the second annular shield 8 being stationary in use.

The annular sealing element 9 has at least a first annular sealing lip 13 and a second annular sealing lip 14; both of the lips 13 and 14 project axially and radially from the second shield 8 towards the first shield 7 and are therefore arranged to be inclined relative to the axis A, so as to diverge from the axis A on the side facing the first shield 7.

According to a first characteristic of the invention, the first annular shield 7 provides a peripheral section 15 radially opposite to the first mounting section 11 and having a first and a second axially extending sleeve portion, indicated respectively by the reference numerals 16 and 18, connected to each other by a radially extending first flange portion 19. The first sleeve portion 16 is radially closer to the first mounting section 11 than the second sleeve portion 18, and the first flange portion 19 forms with the first sleeve portion 16 a step 20 arranged radially inside the first annular shield 7 and facing the second annular shield 8 and the annular sealing element 9.

According to a characteristic of the invention, the annular sealing element 9 is supported by the second shield 8 on a first side 21 of the latter, facing the first shield 7.

In combination with the above arrangement, the second annular shield 8 provides a support section 22, radially opposite to the second mounting section 12 and comprising a second flange portion 23 radially extending towards the first mounting section 11 and carrying the first and second annular sealing lip 13, 14 and a frustoconical intermediate portion 24, which connects the second flange portion 23 to the second mounting portion 12, and which radially and axially projects from the second mounting portion 12 towards the first mounting portion 11. The frustoconical intermediate portion 24 is oriented having an edge connecting to the second mounting section 12 being axially closer to the second bearing part 4 respective to an edge of the frustoconical intermediate portion 24 connecting to the second flange portion 23. The frustoconical intermediate portion 24 and the second flange portion 23 are collectively referred to as carrier section.

The intermediate portion 24 is partially arranged radially within the first sleeve portion 16, is directed radially inwards, and is positioned axially at the step 20 formed by the first flange portion 19 and by the first sleeve portion 16; the intermediate portion 24 is also arranged radially (that is to say, with respect to a radial direction) between the step 20 and the second flange portion 23.

The second mounting section 12 is arranged radially on the inside of the second sleeve portion (that is to say, it is positioned in a radial direction closer to the axis A than the sleeve portion 18) and is arranged at least partially within the second sleeve portion 18.

According to a characteristic of the invention, the second mounting section 12 provides a third flange portion 25 extending radially from the intermediate frustoconical portion 24 and a third sleeve portion 26 extending axially from the third flange portion 25 on the side opposite to the first shield 7, and is arranged radially adjacent to the second sleeve portion 18.

A corresponding sleeve portion 27 of the annular sealing element 9 completely covers the third sleeve portion 26 on the side facing the first shield 7, and forms with the second sleeve portion 18 a radial space 28 which defines, along the whole length of respective sections of the second and third sleeve portions 18 and 26, these sections being axially superimposed (in the sense that they occupy the same axial position in different radial positions), an axially directed labyrinth seal, indicated by the same reference numeral 28.

According to a further characteristic of the invention, the sleeve portion 27 of the annular sealing element 9 axially extends beyond the third sleeve portion 26 of the shield 8, on the side opposite to the first flange portion 19, forming an end section 29 of the annular sealing element 9, which projects free of support from an end edge 30 of the third sleeve portion 26.

According to yet another characteristic of the invention, which is preferred, the sleeve portion 27 of the annular sealing element 9 includes a radially outstanding annular spur 31 arranged at the end edge 30 of the third sleeve portion 26 and flanking the axially extending labyrinth seal 28; the annular spur 31 projects radially from the sleeve portion 27 of the annular sealing element 9 beyond the second sleeve portion 18 and is arranged adjacent to an end edge 32 of the second sleeve portion 18 to form therewith a radially directed labyrinth seal 33.

A root portion 34 of the annular spur 31 axially extends at least in part over a root portion 35 of the end section 29 of the annular sealing element 9 and constitutes a stiffening thickening thereof.

A second side 36 of the second shield 12, opposite to the first side 21, is, at least at the second mounting section 12, completely free of the annular sealing element 9, so that the mounting section 12 is designed to couple in use with a radially outer section 37 of the second bearing part 4, in direct contact therewith and radially on the outside thereof; the third flange portion 25 therefore delimits on its second side 36 a shoulder surface 38 designed to make, in use, axial contact with a frontal surface 39 of the second bearing part 4.

The axially oriented labyrinth seal 28 is arranged radially on the outside of the first and second annular sealing lips 13, 14 to protect them from external contaminants, the first and second sealing lips 13, 14 are also arranged inside the first sleeve portion 16 radially between the sleeve portion 16 and the first mounting section 11.

According to the illustrated preferred embodiment, the annular sealing element 9 entirely covers the second shield 8 on the first side 21 thereof; the first annular sealing lip 13 extends radially outwards from the second flange portion 23 at a junction between the intermediate portion 24 and the second flange portion 23, with an inclination with respect to the axis of symmetry A opposite to that of the intermediate frustoconical portion 24; consequently, the first annular sealing lip 13 forms in radial section a V shape with the intermediate portion 24 and a section of the sealing element 9 which covers the intermediate portion 24, the vertex of the V being arranged substantially at the step 20 or axially slightly inside the first sleeve portion 16.

The first sealing lip 13, in the illustrated preferred embodiment, is a non-contacting lip which forms a labyrinth seal 40 with the first shield 7; the second sealing lip 14, on the other hand, is a contacting lip which forms a sliding "dynamic" seal with the first mounting section 11.

The first mounting section 11 provides a fourth sleeve portion 41 designed to couple, in use, radially on the outside of the first bearing part 3, a fourth flange portion 42 facing the second flange portion 23 and joining at an angle, preferably at a right angle, the first sleeve portion 16, and an inclined, frustoconical connecting portion 43 joining the fourth flange portion 42 with the fourth sleeve portion 41; the labyrinth seal 40 formed by the first sealing lip 13 with the first shield 7 is a dual radial-axial labyrinth seal, formed at the angle between the first sleeve portion 16 and the fourth flange portion 42.

The second sealing lip 14 interacts in a sliding manner with the inclined connecting portion 43 of the mounting section 11; additionally, a third sealing lip 44 is optionally provided on the sealing element 9 to interact in a non-contacting manner with the fourth sleeve portion 41.

From the above description it is evident that the present invention also relates to a rolling bearing 2 equipped with the sealing device 1 fitted between the first and the second bearing part 3, 4; the two bearing parts 3, 4 are rotatable relative to each other about an axis of symmetry A of the sealing device 1 and form between them both an axial space and a radial space with respect to the axis of symmetry A.

The first sleeve portion 16 is arranged within the axial space between the bearing parts 3, 4, while the second sleeve portion 18 extends radially on the outside of the second bearing part 4.

The end section 29 of the annular sealing element 9 which projects free of support from the end edge 30 of the third sleeve portion 26 is arranged flush with an inner lateral surface 45 of the third sleeve portion 26.

The mounting section 12 which is bare, that is to say not covered by the sealing element 9, on the second side 36 is coupled with a metal-to-metal contact to the bearing part 4.

In particular, the third sleeve portion 26 is coupled with a metal-to-metal contact to the radially outer section 37 of the second bearing part 4, which is radially outside it; and the third flange portion 25, which delimits on the second side 36 the shoulder surface 38, is coupled with a metal-to-metal contact to the front surface 39 of the second bearing part 4.

The radially outer section 37 of the second bearing part 4 is formed as an annular depression 46 on an outer lateral surface 47 of the second bearing part 4; the annular depression 46 also receives the end section 29 of the annular sealing element 9, this end section 29 being coupled in a substantially flush manner to the outer lateral surface 47.

Thus an improved seal to friction ratio is obtained: in the first place, the labyrinth seal 28, being directed axially, is less liable to receive external contaminants directly; moreover, the labyrinth function is considerably improved by the presence of the annular spur or projection 31, and by the specific shape of the peripheral section 15 of the shield 7, which acts as a deflector against external contaminants.

The friction is also reduced, and the sealing action improved, by the shape and position of the non-contacting sealing lip 13, which, on the one hand, provides a combined radial-axial labyrinth seal because of its positioning at the right-angle junction between the sleeve portion 16 and the flange portion 42, and which, on the other hand, forms, together with the intermediate portion 24 flanking it, which is inclined in the opposite direction to the lip 13, a collecting channel for any water and contaminants that may pass through the labyrinth seal 28. The contaminants are collected in a highly efficient manner, both because of the presence of the combined labyrinth seal 40 and because the annular collecting channel formed by the lip 13 and the intermediate portion 24 is arranged (in radial section) immediately below the step 20, which acts as a "drip guard"; the collected contaminants may therefore be discharged, by gravity and by the rotation of the shield 7, through the radial space 28.

A better axial positioning of the shield 8 carrying the sealing element is also achieved, with a reduction of the variation in the contact pressure of the contacting lip 14 and a reduction of the friction generated by this lip.

Finally, there is also an increase in the contact pressure of the static seal provided against the outer ring 4 by the end section 29, because of the increased stiffness due to the presence and positioning of the rubber spur or projection 31.

Since the shield 8 is mounted on the outer lateral surface of the outer ring 4, there is also a reduction of the axial overall dimensions of the wheel and hub assembly 5, with a considerable reduction in weight, which is achieved, in particular, by the shape of the shield 8, and specifically by the presence of the conically shaped intermediate portion 24 which carries the sealing lips at a distance from the rolling bodies 10. The amount of grease required is also reduced, and its distribution is improved in operating conditions. Reduction in the dimensions is also achieved as a result of a portion of the rolling bodies and a portion of the second mounting section of the second annular shield passing through a same radially oriented plane.

All the objects of the invention are therefore achieved.

The invention claimed is:

1. A sealing device for sealing a rolling bearing between a first bearing part and a second bearing part that form a wheel hub assembly, the first bearing part and second bearing part being rotatable relative to each other around an axis of symmetry (A) of the sealing device, the sealing device comprising:
    a first annular shield having a first mounting section for attachment to the first bearing part, the first annular shield rotating around the symmetry axis (A);
    a second annular shield coaxial with the first annular shield and having a second mounting section for attachment to the second bearing part, the second annular shield being stationary; and
    an annular sealing element made of an elastomeric material and integrally supported by the second annular shield, the annular sealing element having at least a first annular sealing lip and a second annular sealing lip axially and radially projecting from the second annular shield toward the first annular shield;
    wherein the first annular shield provides a peripheral section radially opposite to the first mounting section and having a first axially extending sleeve portion and a second axially extending sleeve portion connected to each other by a radially extending first flange portion, the first sleeve portion radially closer to the first mounting section than the second sleeve portion and the first flange portion forming with the first sleeve portion a step arranged radially inside the second axially extending sleeve portion and facing the second annular shield and the annular sealing element, which is supported by the second annular shield on a first side thereof facing the first annular shield;
    wherein the second annular shield provides a carrier section radially opposite to the second mounting section, the carrier section comprising a second flange portion radially extending towards the first mounting section and carrying the first annular sealing lip and the second annular sealing lip and a frustoconical intermediate portion connecting the second flange portion to the second mounting portion and radially and axially projecting from the second mounting portion towards the first mounting portion, the frustoconical intermediate portion being arranged partially radially inside of the first sleeve portion, the frustoconical intermediate portion being directed radially inwards and axially positioned at the step formed by the first flange portion and the first sleeve portion, the frustoconical intermediate portion being arranged radially between the step and the second flange portion, the frustoconical intermediate portion being oriented having an edge connecting to the second mounting section being axially closer to the second bearing part respective to than an edge of the frustoconical intermediate portion connecting to the second flange portion; and
    wherein the second mounting section is arranged radially on the inside of the second sleeve portion and partly within the second sleeve portion, the second mounting section comprising a third flange portion extending radially from the frustoconical intermediate portion and a third sleeve portion extending axially from the third flange portion on the side opposite to the first annular shield and arranged radially adjacent to the second sleeve portion;
    a corresponding sleeve portion of the annular sealing element completely covering the third sleeve portion on the side facing the first annular shield and forming with the second sleeve portion a radial gap defining along the whole length of axially superimposed stretches of the second and third sleeve portion an axially oriented labyrinth seat, wherein a series of rolling bodies are assembled between the first bearing part and the second bearing part at a location where at least a portion of each rolling body of the series of rolling bodies and a portion of the second mounting section of the second annular shield pass through a same radially oriented plane.

2. The sealing device according to claim 1, wherein the sleeve portion of the annular sealing element axially extends beyond the third sleeve portion on the side opposite to the first flange portion forming an end section of the annular sealing element projecting free of support from an end edge of the third sleeve portion.

3. The sealing device according to claim 2, wherein the sleeve portion of the annular sealing element includes a radially outstanding annular spur arranged at the end edge of the third sleeve portion and flanking the axially extending labyrinth seal; the annular spur projecting radially from the sleeve portion of the annular sealing element beyond the second sleeve portion and being arranged adjacent to an end edge of the second sleeve portion to form therewith a radially directed labyrinth seal.

4. The sealing device according to claim 3, further comprising a first root portion and a second root portion, wherein the first root portion is part of the annular spur and wherein the second root portion is part of the end section of the annular sealing element, wherein the first root portion axially extends at least in part over the second root portion, wherein a thicker and stiffer section is formed where the first root portion extends axially over the second root portion compared to where the first root portion does not extend over the second root portion.

5. The sealing device according to claim 1, further comprising a second side of the second annular shield, opposite to the first side, that is at least at the second mounting section completely free of the annular sealing element and configured to couple with a radially outer stretch of the second bearing part, in direct contact therewith and radially on the outside thereof; the third flange portion delimiting on the second side a shoulder surface designed to make axial contact with a frontal surface of the second bearing part.

6. The sealing device according to claim 1, wherein the axially oriented labyrinth seal is arranged radially on the outside of the first annular sealing lip and the second annular sealing lip to protect them from outer contaminants, the first annular sealing lip and the second annular sealing lip being arranged inside the first sleeve portion radially between the first sleeve portion and the first mounting section.

7. The sealing device according to claim 1, wherein the annular sealing element covers the second annular shield on the first side; the first annular sealing lip extending radially outwards from the second flange portion at a junction between the frustoconical intermediate portion and the second flange portion of the carrier section; wherein the first annular sealing lip includes at least one of:

(a) an inclination with respect to the symmetry axis (A) that is opposite the frustoconical intermediate portion;

(b) the first annular sealing lip forming in radial section a V with the frustoconical intermediate portion and a portion of the sealing element covering the frustoconical intermediate portion, a vertex of the V being arranged substantially at a same axial position of a step formed by the first flange portion and the first sleeve portion or radially inward and proximate the first sleeve portion;

(c) the first annular sealing lip being a non-contacting lip forming a labyrinth seal with the first annular shield and the second annular sealing lip being a contacting lip forming a sliding dynamic seal with the first mounting section.

8. The sealing device according to claim 7, wherein the first mounting section provides a fourth sleeve portion configured to couple radially on the outside of the first bearing part, a fourth flange portion facing the second flange portion and joining at an angle, the first sleeve portion, and an inclined, frustoconical shaped connecting portion joining the fourth flange portion with the fourth sleeve portion; the first annular sealing lip forming a dual, radial-axial labyrinth seal with the first annular shield at the angle between the first sleeve portion and the fourth flange portion and the second annular sealing lip cooperating in sliding manner with the inclined frustoconical shaped connecting portion of the mounting section; a third annular sealing lip being optionally provided on the sealing element to cooperate in a non-contacting manner with the fourth sleeve portion.

9. A rolling bearing having a sealing device between a first bearing part and a second bearing part for forming a wheel hub assembly, the first bearing part and the second bearing part being rotatable relative to each other around an axis of symmetry (A) of the sealing device and forming therebetween both an axial space and a radial space with respect to the axis of symmetry, the sealing device comprising:

a first annular shield having a first mounting section for attachment to the first bearing part, the first annular shield rotating around the symmetry axis;

a second annular shield coaxial with the first annular shield and having a second mounting section for attachment to the second bearing part, the second annular shield being stationary; and an annular sealing element made of an elastomeric material and integrally carried by the second annular shield, the annular sealing element having at least a first annular sealing lip and a second annular sealing lip axially and radially projecting from the second annular shield toward the first annular shield;

wherein the first annular shield provides a peripheral section radially opposite to the first mounting section and having a first axially extending sleeve portion and a second axially extending sleeve portion connected to each other by a radially extending first flange portion, the first sleeve portion being radially closer to the first mounting section than the second sleeve portion and the first flange portion forming with the first sleeve portion a step arranged radially inside the second axially extending sleeve portion and facing the second annular shield and the annular sealing element, which is supported by the second annular shield on a first side thereof facing the first annular shield;

wherein the first sleeve portion is housed within the axial space while the second sleeve portion extends radially on the outside of the second bearing part;

wherein the second annular shield provides a carrier section radially opposite to the second mounting section, the carrier section comprising a second flange portion radially extending towards the first mounting section and carrying the first annular sealing lip and the second annular sealing lip and a frustoconical intermediate portion connecting the second flange portion to the second mounting portion and radially and axially projecting from the second mounting portion towards the first mounting portion within the axial space, the frustoconical intermediate portion being arranged partially radially inside of the first sleeve portion, the frustoconical intermediate portion being directed radially inwards and axially positioned at the step formed by the first flange portion and the first sleeve portion, the frustoconical intermediate portion being arranged radially between the step and the second flange portion, the frustoconical intermediate portion being oriented having an edge connecting to the second mounting section being axially closer to the second bearing part than an edge of the frustoconical intermediate portion connecting to the second flange portion; and wherein the second mounting section is arranged radially on the inside of the second sleeve portion and partly within the second sleeve portion, the second mounting section comprising a third flange portion extending radially from the frustoconical intermediate portion and a third sleeve portion extending axially from the third flange portion on the side opposite to the first annular shield and arranged radially adjacent to the second sleeve portion;

a corresponding sleeve portion of the annular sealing element covering the third sleeve portion on the side facing the first annular shield and forming with the second sleeve portion a radial gap defining along the whole length of axially superimposed stretches of the second and third sleeve portion an axially oriented labyrinth seal, wherein a series of rolling bodies are assembled between the first bearing part and the second bearing part at a location where at least a portion of each rolling body of the series of rolling bodies and a portion of the second mounting section of the second annular shield pass through a same radially oriented plane.

10. The sealing device according to claim 9, wherein the sleeve portion of the annular sealing element axially extends beyond the third sleeve portion on the side opposite to the first flange portion forming an end section of the annular sealing element projecting free of support from an end edge of the third sleeve portion and arranged flush with a lateral inner surface of the third sleeve portion; the sleeve portion of the annular sealing element including a radially outstanding annular spur arranged at the end edge of the third sleeve portion and flanking the axially extending labyrinth seal; the annular spur projecting radially from the sleeve portion of the annular sealing element and being arranged adjacent to an end edge of the second sleeve portion to form therewith a radially directed labyrinth seal.

11. The sealing device according to claim 10, further comprising a second side of the second annular shield, opposite to the first side, is at least at the second mounting section completely free of the annular sealing element and couples with a metal to metal contact with a radially outer stretch of the second bearing part radially on the outside thereof; the third flange portion delimiting on the second side a shoulder surface in axial metal to metal contact with a frontal surface of the second bearing part; the radially outer stretch of the second bearing part being formed as an annular recess on an outer lateral surface of the second bearing part, the annular recess also receiving the end section of the annular sealing element that is flush with the outer lateral surface of the second bearing part.

12. The sealing device according to claim 9, wherein the first mounting section provides a fourth sleeve portion configured to couple radially on the outside of the first bearing part, a fourth flange portion facing the second flange portion and joining at a right angle, the first sleeve portion, and an inclined, frustoconical shaped connecting portion joining the fourth flange portion with the fourth sleeve portion; the first annular sealing lip forming a dual, radial-axial labyrinth seal with the first annular shield at the angle between the first sleeve portion and the fourth flange portion and the second annular sealing lip cooperating in sliding manner with the inclined frustoconical shaped connecting portion of the mounting section; a third sealing lip being optionally provided on the sealing element to cooperate in a non-contacting manner with the fourth sleeve portion.

13. A sealing device for sealing a rolling bearing between a first bearing part and a second bearing part that form a wheel hub assembly, the first bearing part and second bearing parts being rotatable relative to each other around an axis of symmetry (A) of the sealing device, the sealing device comprising:

a first annular shield having a first mounting section for attachment to the first bearing part, the first annular shield rotating around the symmetry axis (A);

a second annular shield coaxial with the first annular shield and having a second mounting section for attachment to the second bearing part, the second annular shield being stationary; and an annular sealing element made of an elastomeric material and integrally supported by the second annular shield, the annular sealing element having at least a first annular sealing lip and a second annular sealing lip axially and radially projecting from the second annular shield toward the first annular shield;

wherein the first annular shield provides a peripheral section radially opposite to the first mounting section and having a first axially extending sleeve portion and a second axially extending sleeve portion connected to each other by a radially extending first flange portion, the first sleeve portion radially closer to the first mounting section than the second sleeve portion and the first flange portion forming with the first sleeve portion a step arranged radially inside the second axially extending sleeve portion and facing the second annular shield and the annular sealing element, which is supported by the second annular shield on a first side thereof facing the first annular shield;

wherein the second annular shield provides a carrier section radially opposite to the second mounting section, the carrier section comprising a second flange portion radially extending towards the first mounting section and carrying the first annular sealing lip and the second annular sealing lip and a frustoconical intermediate portion connecting the second flange portion to the second mounting portion and radially and axially projecting from the second mounting portion towards the first mounting portion, the frustoconical intermediate portion being arranged partially radially inside of the first sleeve portion, the frustoconical intermediate portion being directed radially inwards and axially positioned at the step formed by the first flange portion and the first sleeve portion, the frustoconical intermediate portion being arranged radially between the step and the second flange portion; and wherein the second mounting section is arranged radially on the inside of the second sleeve portion and partly within the second sleeve portion, the second mounting section comprising a third flange portion extending radially from the frustoconical intermediate portion and a third sleeve portion extending axially from the third flange portion on the side opposite to the first annular shield and arranged radially adjacent to the second sleeve portion;

a corresponding sleeve portion of the annular sealing element completely covering the third sleeve portion on the side facing the first annular shield and forming with the second sleeve portion a radial gap defining along the whole length of axially superimposed stretches of the second and third sleeve portion an axially oriented labyrinth seal wherein the annular sealing element covers the second annular shield on the first side; the first annular sealing lip extending radially outwards from the second flange portion at a junction between the frustoconical intermediate portion and the second flange portion of the carrier section; wherein the first annular sealing lip includes at least one of:

(a) an inclination with respect to the symmetry axis (A) that is opposite the frustoconical intermediate portion;
(b) the first annular sealing lip forming in radial section a V with the frustoconical intermediate portion and a portion of the sealing element covering the frustoconical intermediate portion, a vertex of the V being arranged substantially at a same axial position of a step formed by the first flange portion and the first sleeve portion or radially inward and proximate the first sleeve portion;
(c) the first annular sealing lip being a non-contacting lip forming a labyrinth seal with the first annular shield and the second annular sealing lip being a contacting lip forming a sliding dynamic seal with the first mounting section.

14. The sealing device according to claim 13, wherein the first mounting section provides a fourth sleeve portion configured to couple radially on the outside of the first bearing part, a fourth flange portion facing the second flange portion and joining at an angle, the first sleeve portion, and an inclined, frustoconical shaped connecting portion joining the fourth flange portion with the fourth sleeve portion; the first annular sealing lip forming a dual, radial-axial labyrinth seal with the first annular shield at the angle between the first sleeve portion and the fourth flange portion and the second annular sealing lip cooperating in sliding manner with the inclined frustoconical shaped connecting portion of the mounting section; a third sealing lip being optionally provided on the sealing element to cooperate in a non-contacting manner with the fourth sleeve portion.

15. The sealing device according to claim 13, wherein the first mounting section provides a fourth sleeve portion configured to couple radially on the outside of the first bearing part, a fourth flange portion facing the second flange portion and joining at a right angle, the first sleeve portion, and an inclined, frustoconical shaped connecting portion joining the fourth flange portion with the fourth sleeve portion; the first annular sealing lip forming a dual, radial-axial labyrinth seal with the first annular shield at the angle between the first sleeve portion and the fourth flange portion and the second annular sealing lip cooperating in sliding manner with the inclined frustoconical shaped connecting portion of the mounting section; a third sealing lip being optionally provided on the sealing element to cooperate in a non-contacting manner with the fourth sleeve portion.

* * * * *